United States Patent [19]

Shikani et al.

[11] Patent Number: 5,695,458
[45] Date of Patent: Dec. 9, 1997

[54] ANTI-INFECTIVE POLYMER-IODINE COATING FOR BLOOD COLLECTION AND DELIVERY SYSTEMS

[75] Inventors: Alan H. Shikani, Ruxton, Md.; Abraham J. Domb, Efrat, Israel

[73] Assignee: Maryland Biopolymer Technologies, LLC, Towson, Md.

[21] Appl. No.: 641,518

[22] Filed: May 1, 1996

Related U.S. Application Data

[63] Continuation-in-part of Ser. No. 601,251, Feb. 14, 1996, which is a continuation-in-part of Ser. No. 316,067, Sep. 30, 1994, Pat. No. 5,512,055, which is a continuation of Ser. No. 998,773, Dec. 22, 1992, abandoned, which is a continuation of Ser. No. 661,699, Feb. 27, 1991, abandoned.

[51] Int. Cl.$^6$ ............................................. A61M 37/00
[52] U.S. Cl. ................................. 604/4; 427/2.12
[58] Field of Search ........................... 604/4–6, 264, 604/280, 265; 128/207.14, 207.15; 623/1, 11, 12; 422/28, 40, 41; 427/2.12

[56] References Cited

U.S. PATENT DOCUMENTS

| | | | |
|---|---|---|---|
| 3,235,446 | 2/1966 | Shelanski et al. | 167/17 |
| 4,094,967 | 6/1978 | Gilbert | 424/28 |
| 4,381,380 | 4/1983 | LeVeen et al. | 525/452 |
| 4,879,135 | 11/1989 | Greco et al. | 427/2 |
| 4,917,686 | 4/1990 | Bayston et al. | 604/265 |
| 4,950,256 | 8/1990 | Luther et al. | 604/265 |
| 4,994,047 | 2/1991 | Walker et al. | 604/264 |
| 5,019,096 | 5/1991 | Fox, Jr. et al. | 623/1 |
| 5,071,648 | 12/1991 | Rosenblatt | 424/78.06 |
| 5,512,055 | 4/1996 | Domb et al. | 604/265 |

*Primary Examiner*—John G. Weiss
*Assistant Examiner*—Ki Yong O
*Attorney, Agent, or Firm*—Leonard Bloom

[57] ABSTRACT

A body fluid collection, storage and transfusion system which contains a polymer-iodine coating to destroy toxic microorganisms. The system is intended to be used to disinfect blood or blood products, as well as urine, wound exudates, serum, plasma, drainage fluids and synovial fluids.

2 Claims, 9 Drawing Sheets

ANTI-INFECTIVE POLYMER-IODINE COATING FOR BLOOD COLLECTION AND DELIVERY SYSTEMS

CROSS REFERENCE TO RELATED APPLICATIONS

The present invention is a continuation-in-part of application Ser. No. 08/601,251, pending, filed Feb. 14, 1996 which, in turn, was a continuation-in-part of application, Ser. No. 08/316,067 filed Sep. 30, 1994, U.S. Pat. No. 5,512,055 which was a continuation of Ser. No. 07/998,773 filed Dec. 22, 1992 (now abandoned), and which was a continuation of Ser. No. 07/661,699 filed Feb. 27, 1991 (now abandoned), the disclosures of which are hereby incorporated herein in their entirety.

BACKGROUND OF THE INVENTION

A longstanding problem in the area of hospital and laboratory equipment, as well as patient care items that have come in contact with body fluids, is their potential to infect patients, hospital personnel, and, if released in the environment, to infect the general public. Two pathogenic organisms that have the potential for infecting patients are the HIV and the hepatitis B virus. These viruses are, more and more, becoming a serious public health problem because of the logarithmic increase in the number of people infected with either of these two viruses. Although the HIV is not capable of withstanding exposure to a wide range of temperature and humidity changes, it is still stable enough to remain viable and retain infectivity for more than three days if dried and held at room temperature; and for more than a week in an aqueous environment at room temperature. The hepatitis B virus (HBV) is even more resistant and remains viable at room temperature for 6 months. This means that any patient care item, that has come in contact with body fluids from infected individuals, is potentially infective if the milieu is kept relatively moist. Unless the viruses are inactivated, the contaminated medical devices will present a significant public health hazard.

The prior art has recognized the use of iodine per se to inactivate viruses; and of course iodine is a well known antimicrobial agent. Highsmith et al in *Blood*, Vol. 86, No. 2 (Jul. 15, 1995) pages 791–796 teach the use of iodine to inactivate viruses in blood products. Also shown by the publication is the use of cross-linked polyvinylpyrrolidone-iodine, cross-linked starch-iodine, as well as liquid iodine to inactivate viruses.

There exists, however, a need in the art to collect body fluids and exudates in a safe and efficient manner, free from infective contaminants. The need exists in the blood collection and transfusion art to obtain and supply blood free of infection. Among the diseases transmittable by contaminated blood are HIV and hepatitis along with a variety of other bacterial and viral infections. Particularly alarming is the problem of contaminated blood, and particularly viral contaminated blood used for blood transfusions. HIV contaminated blood is particularly worrisome because many donors are suspected of being HIV positive or may not know that they are HIV positive and yet donate blood for transfusion. Moreover, there is a failure rate in actual testing, wherein the test will produce a false negative. To be considered, also, is the fact that many poorer countries do not have resources for testing blood for viral contamination. While this invention addresses the need in blood collection technology, the invention will find utility in collecting other body fluids and products such as urine, wound exudate, serum, plasma, body drainage fluid, and synovial fluid.

The present inventors have successfully coated medical devices made from different materials. They have successfully coated venous catheters and bladder-Foley catheters, containing polymers and iodine; and demonstrated that the iodine is released in a sustained fashion over prolonged periods of time and inactivates the virus within less than 30 minutes. Among the different materials successfully coated with the iodine containing polymers were polyethylene, silicone, polyvinyl chloride, polyethylene phthalate, polypropylene, rubber, as well as metal including needles and scalpel blades. These inventions made by the applicants are disclosed and claimed in U.S. Pat. Nos. 5,344,411 and 5,437,656 issued on Sep. 6, 1994 and Aug. 1, 1995, respectively.

SUMMARY OF THE INVENTION

The present invention relates to antiinfective coatings for non-implantable medical devices. More specifically this invention relates to antiinfective polymer coatings for medical devices, such as hospital and laboratory equipment. Examples of the specific type of equipment contemplated is equipment used in the collection, storage and transfusion of blood, as well as containers for blood-derived products like serum and plasma. Also contemplated are containers for collecting body fluids such as urine, wound exudate, drainage fluids and synovial fluid.

The herein disclosed invention has as its main object the preparation and the supply of blood collection, storage and transfusion devices having an antiinfective polymer coating.

A further object of this invention is to produce such devices with an antiinfective coating which will kill germs when the coated devices come in contact with said germs.

This invention envisions antiinfective polymer coatings of laboratory equipment and like items, which come into contact with blood. The antiinfective polymer coating can be programmable for the sustained release of an antiinfective agent, as well as for the rapid release of the agent.

More specifically, this invention relates to the use of iodine-loaded polymers to inactivate any potential infective agent that may be present in blood, blood products or body fluids which come into contact with equipment. The infective agents to be treated relate particularly to the HIV (human immunodeficiency virus) and the HBV (hepatitis B virus), as well as to all other potentially pathogenic organisms including viruses such as hepatitis A, hepatitis C, hepatitis E, encephalomyocarditis virus (EMCV), sindbis virus (SINV), pseudorabies virus (PRV), vesicular stomatitis virus (VSV) bacteria, fungi, mycobacteria and spores, which would be inactivated by the iodine compositions of this invention. The equipment coming in contact with blood can be precoated with an iodine containing polymer to start releasing iodine in programmable and sustained fashion for prolonged periods of time, once in contact with infectious fluid, or programmable for quick-release of the iodine. The inventors have performed studies that have proven this technology highly effective in inactivating viruses and pathogenic bacteria.

The herein disclosed invention envisions iodine polymer coatings on containers or receptacles, as for example blood bank equipment (including blood and blood product containers and tubings). Also proposed are containers for collecting urine, wound exudate, drainage fluid and synovial fluid; and blood products such as serum and plasma. The containers can be coated either on the inside or outside; and can have partial coatings.

In a broad aspect this invention involves a blood collection, storage and transfusion system that has a polymer-iodine coated collection container, a polymer-iodine coated storage container and a polymer-iodine coated transfusion container, wherein the iodine from each polymer-iodine coating on the containers comes into contact with blood or a blood product and aids in inactivating toxic microorganisms which may be found in the blood or blood product. Also envisioned by this invention is a method for the safe and effective collection, storage and transfusion of blood comprising, collecting blood from a donor employing a polymer-iodine coated container to receive the blood, then storing said collected blood in a polymer-iodine coated storage container, and then transfusing the blood from a polymer-iodine coated transfusion container, wherein the iodine released from each polymer-iodine coating contacts blood or a blood product and aids in inactivating toxic microorganisms.

Also contemplated by the invention is a blood collection container, wherein the inside of said container is polymer-iodine coated to aid in inactivating toxic microorganisms which may be found in the blood collected therein. The collection container can have a polymer-iodine coated tubing attached thereto.

Additionally, the invention involves a blood storage container having the insides thereof coated with a polymer-iodine coating.

Besides being coated on the inside, the blood or body fluid container can be coated on the outside surface with a polymer-iodine coating such that when a fluid enters and is contained in said container the fluid will permeate to the container surface and leach dissolved iodine into the container from the outside polymer-iodine coating.

Besides the coated blood storage container, the invention supplies a container used to transfuse blood having its inside surface coated with a polymer-iodine coating. The containers described herein can have attached thereto polymer-iodine coated tubing.

An elegant embodiment of this invention contemplates a polymer or other type of film strip or patch containing releasable iodine. The film strip can be made to adhere to the plastic raw material prior to manufacture and form part of the finished container; or the film strip can be added to the blood container prior to, or after, the blood is added thereto and is suspended in the blood or other collected fluid.

After the iodine remains in contact with the blood and/or blood products for about 30 minutes, all viruses and other microorganisms would be inactivated and it would be important to remove the iodine prior to transfusing the blood or blood products to a patient in order to avoid iodine toxicity or other untoward effects related to iodine.

This invention contemplates a system for removing iodine from the transfusion bag. Contemplated is a filter or other such extracting device to which the blood or blood product container can be attached and iodine removed before use of the product.

A unique advantage of the herein disclosed invention is that it offers redundancy. That is, since each receptacle and tube in the system is polymer-iodine coated, there is an added opportunity for the iodine to inactivate any microorganism which may not have been inactivated in a previous step of the blood collection, storage, blood fractionation and/or transfusion process.

Our issued patents referred to above, describe in detail compositions and coating methods for coating catheters and metal instruments, such as scalpel blades. These coating methods and compositions can be employed to coat the blood-contacting articles described herein; and these polymer compositions and coating methods are herein incorporated by reference.

These and other objects of the present invention will become apparent from a reading of the following specification taken in conjunction with the enclosed drawings.

DESCRIPTION

Figure 1:
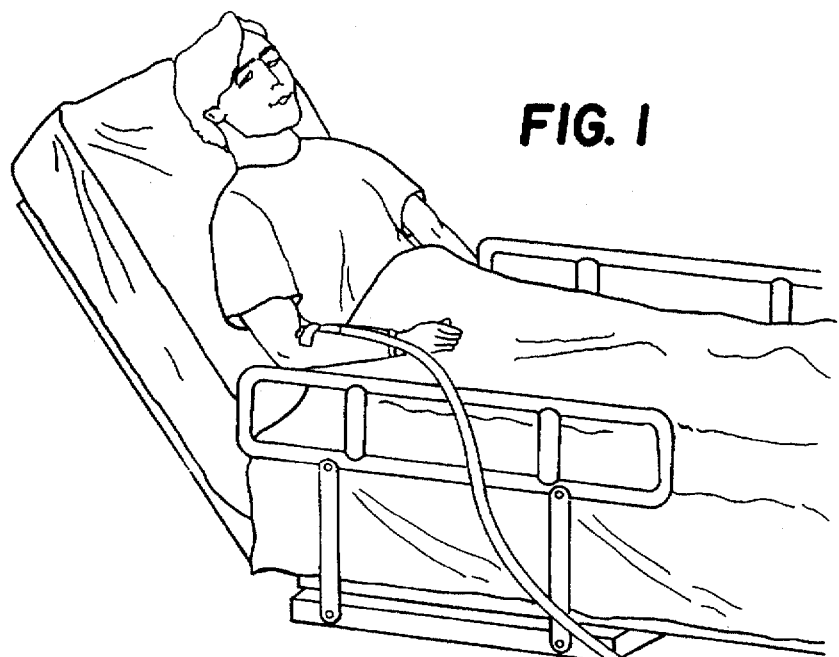
FIG. 1 is a view illustrating a typical blood collection system with a polymer-iodine coated interior.

With reference to FIGS. 1–4, the blood collection system 10 has a rigid receptacle 12 or a flexible receptacle 16 and an internal polymer-iodine coating 14 (not to scale).

Once the plastic blood bottle or rigid receptacle 12 (FIG. 1) or the flexible plastic bag 16 (FIG. 3) are filled, the blood can be stored therein, or the blood can be processed to obtain various blood fractions as is conventional in the art. It is significant to note that the blood processing and storage equipment (e.g. containers and tubing) are polymer-iodine coated, thus ensuring adequate (redundant) contact between blood, blood components, and iodine.

Figure 2:
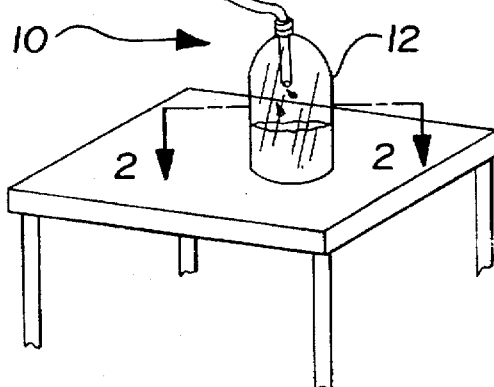
FIG. 2 is a greatly enlarged cross-section taken along lines 2—2 of FIG. 1.
Figure 2:
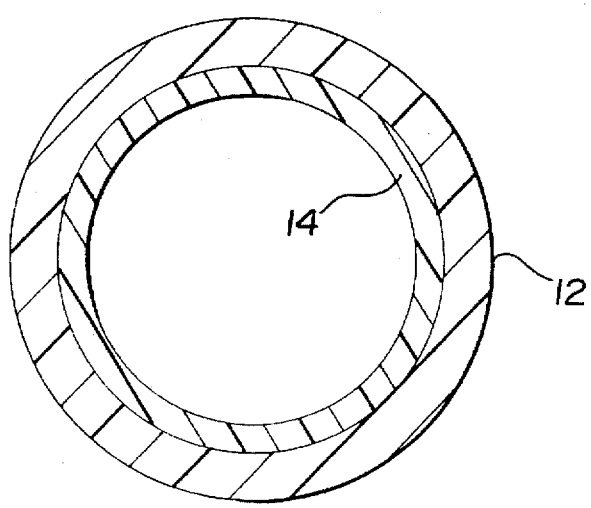
Figure 3:
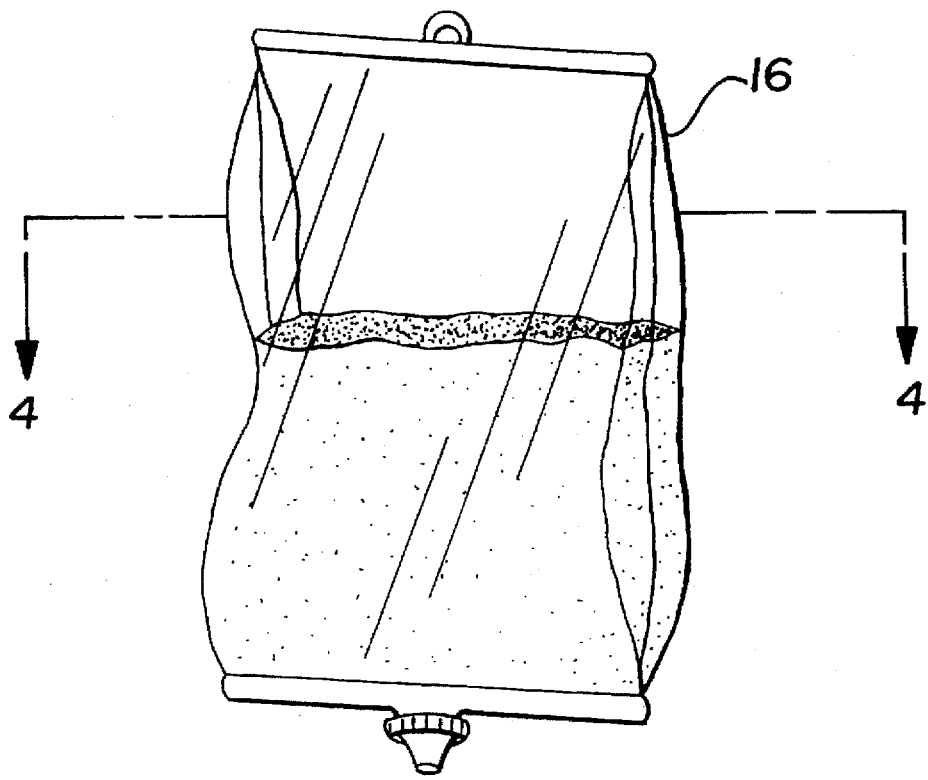
FIG. 3 is a perspective view illustrating a plastic bag blood storage device with a polymer-iodine coated interior.
Figure 4:
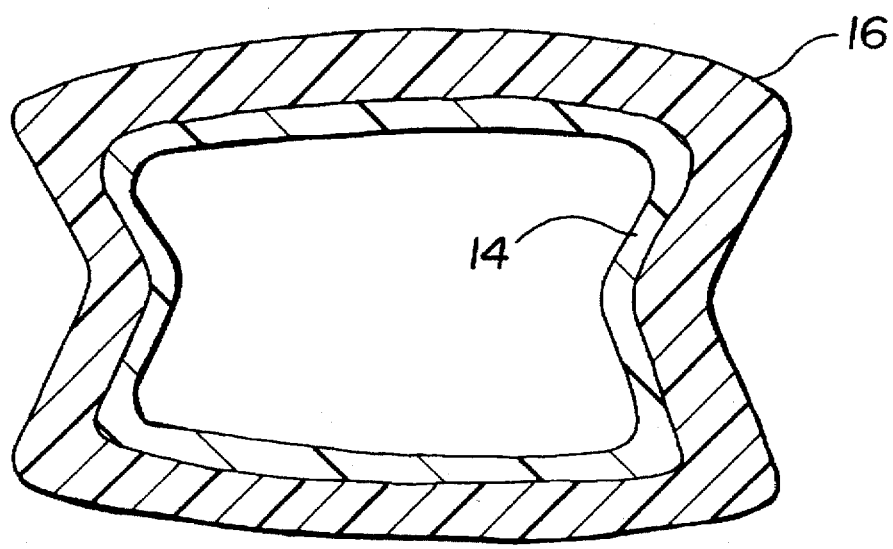
FIG. 4 is an enlarged cross-section taken along lines 4—4 of FIG. 3.

Referring to FIGS. 2 and 4, the rigid container 12 and flexible plastic bag 16 are coated with an iodine containing polymer 14. When coming into contact with the iodine containing polymer 14, the liquid of the blood will cause iodine to leach out of the polymer into the blood to inactivate infectious microorganisms; and particularly infectious viruses that may be present in the blood.

Figure 5:
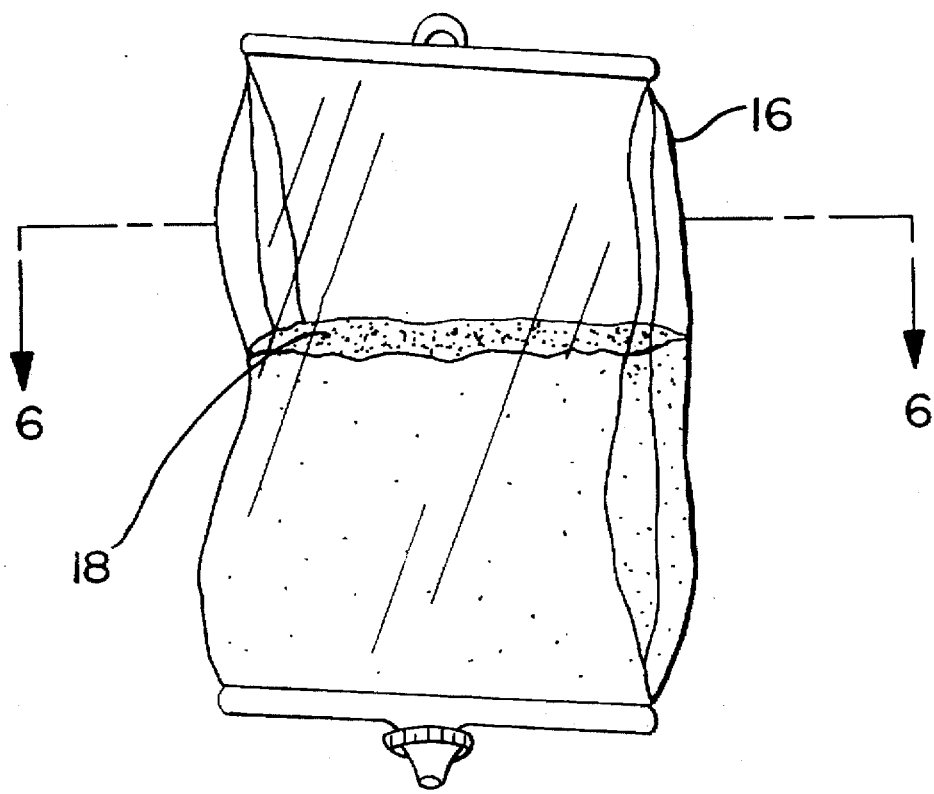
FIG. 5 is a perspective view illustrating a plastic bag blood storage device with a polymer-iodine coated exterior.
Figure 6:
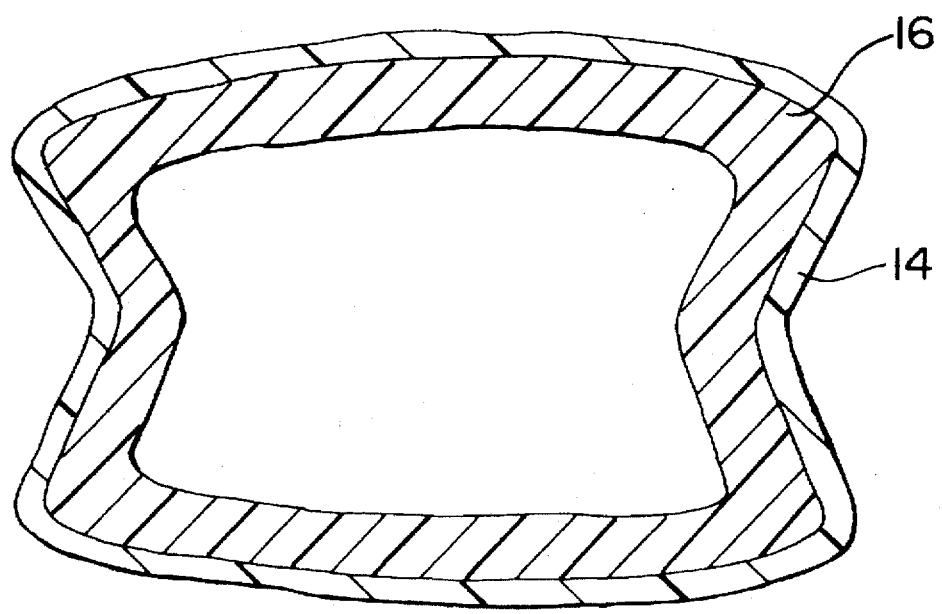
FIG. 6 is an enlarged sectional view taken along lines 6—6 of FIG. 5.
Figure 7:
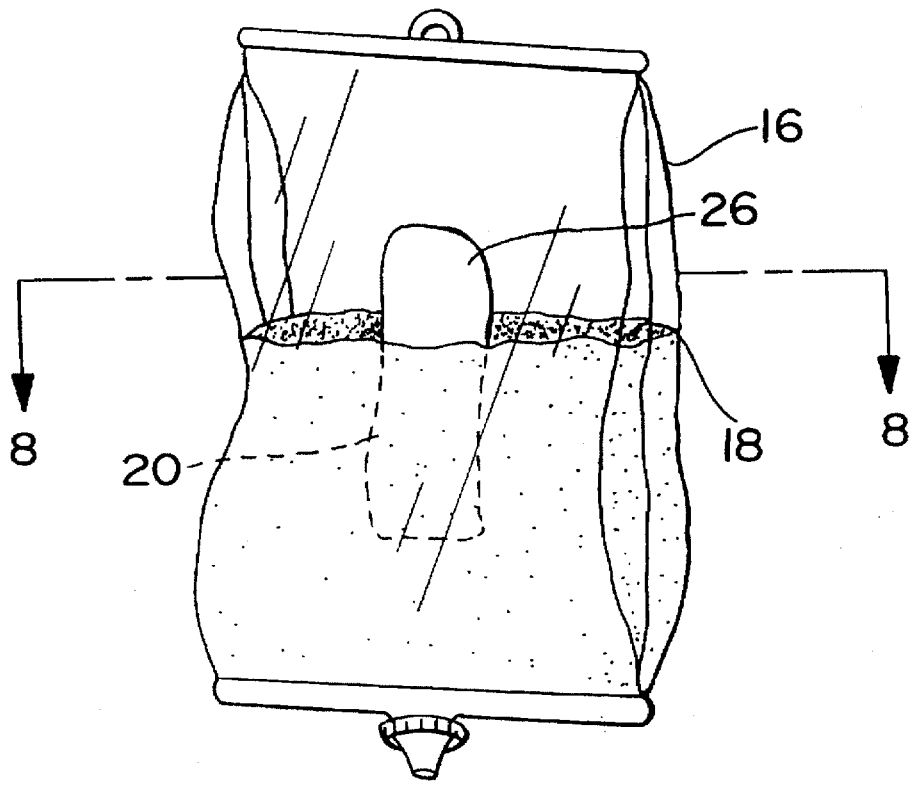
FIG. 7 is a perspective view illustrating a plastic bag blood storage device with a polymer-iodine plastic sticker attached to the inside of the plastic bag.
Figure 8:
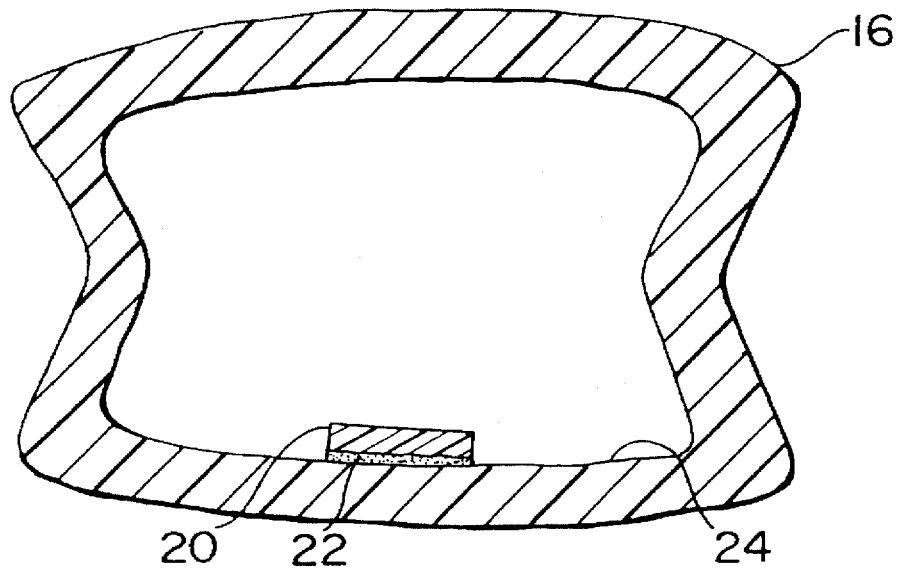
FIG. 8 is a sectional view thereof taken along lines 8—8 of FIG. 7.
Figure 9:
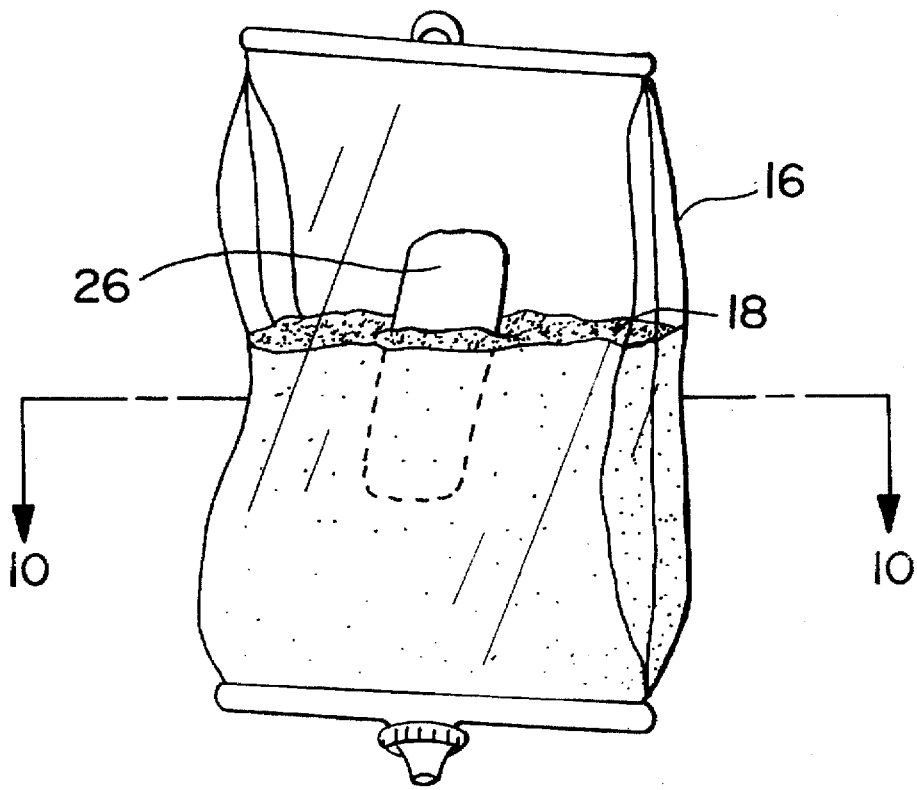
FIG. 9 is a view illustrating a polymer-iodine coated plastic tag suspended in the blood fluid.
Figure 10:
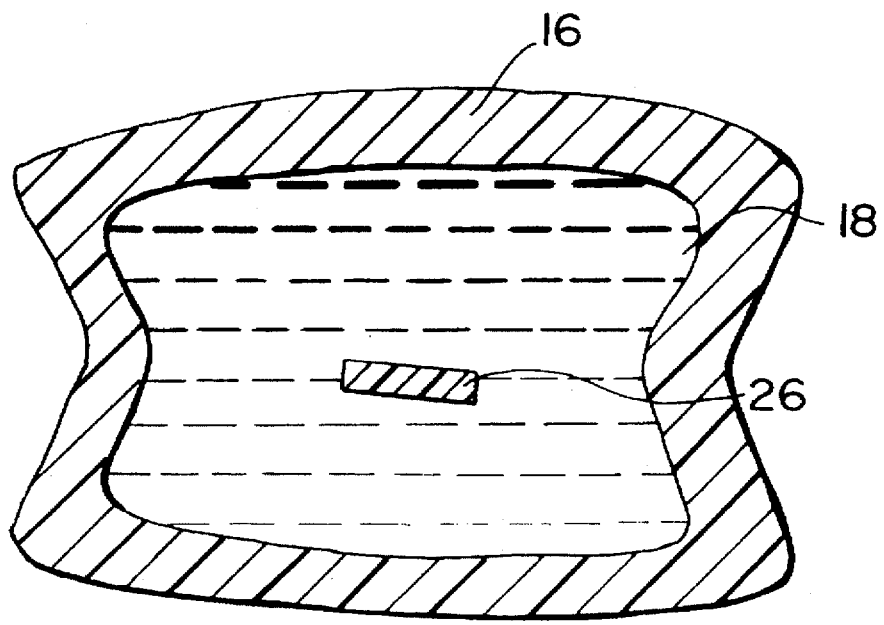
FIG. 10 is a cross-sectional view thereof taken along lines 10—10 of FIG. 9.

The polymer-iodine coating 14 can be formed on the outside of the container 16 and the iodine can be caused to leach through the external plastic wall of the container into the blood 18 in the container (FIGS. 5 and 6). While a flexible receptacle has been shown the outer polymer-iodine coating could be applied to a rigid plastic receptacle or the like.

With reference to FIGS. 7–10 an alternative to the iodine polymer coatings 14, a tag 20 containing polymer-iodine can be attached with adhesive 22 to the inner surface 24 of the container 16 (FIGS. 7–8) or as an insert 26 suspended in the blood fluid 18 (FIGS. 9–10) to supply the antiinfective amount of iodine to the blood 18.

Figure 11:
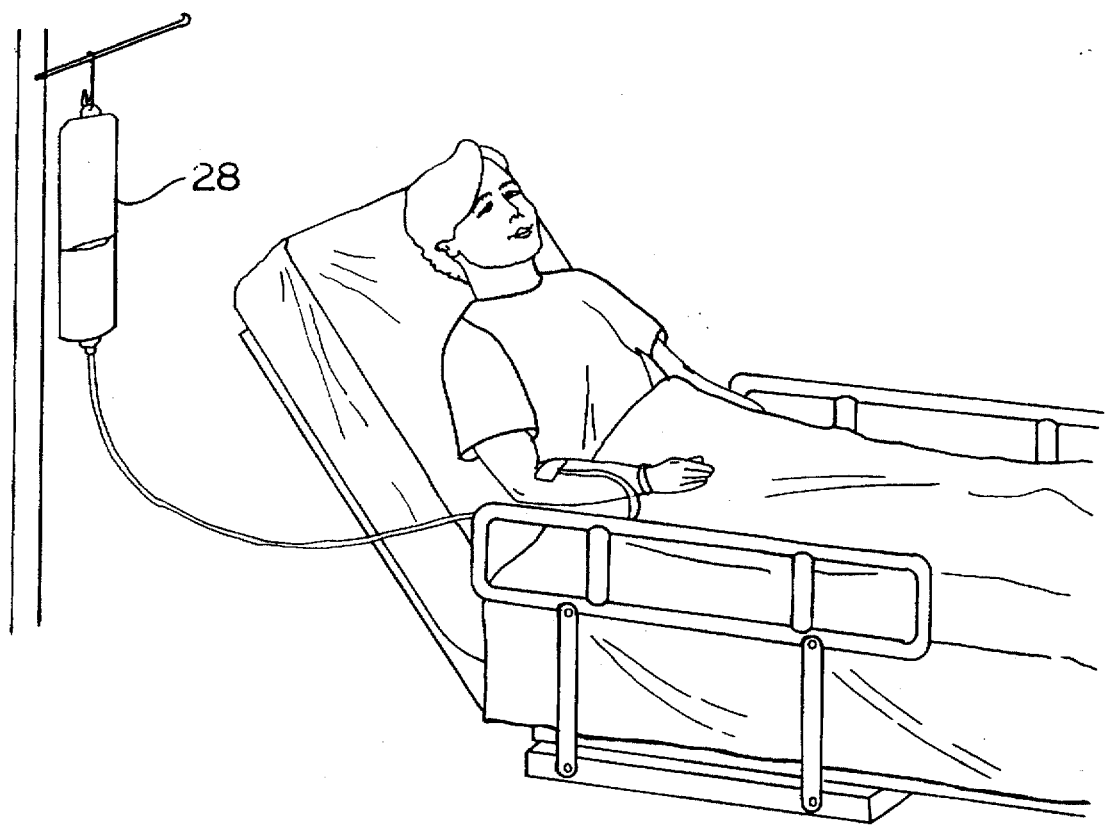
FIG. 11 is a view illustrating blood being transfused into a patient using a polymer-iodine coated transfusion container.

When required, the stored blood or blood fraction product can be transfused to the patient in need thereof (FIG. 11), using a coated transfusion container or bag 28.

While FIGS. 1–11 are directed to blood collection containers, the teachings of this invention are applicable to containers for urine, wound exudates, body drainage fluids, synovial fluid, serum and plasma.

It is important to bear in mind that the blood or other containers of this invention for optimum results should have all or substantially all of the surface coming into contact with the fluid coated with iodine polymer composition. Of importance also is the fact that the polymers of this invention do not swell to any substantial degree; they are not hydrogels and may absorb less that 10% water.

In general, the plastic of the containers do not require priming before polymer application; the polymer iodine compositions of this invention are designed to adhere to the container or bag surface.

The invention contemplates an anti-infective coating for body fluid containers. The coating is a biocompatible, non-hydrogel polymer. One embodiment is a coating which is complexed with an iodine solution to provide a programmed rapid release of iodine. A second embodiment is a solution of the biocompatible polymer in which the iodine is dissolved and the solution containing iodine is coated to provide a matrix having programmed sustained release of iodine. A coating with complexed iodine may be deposited over a coating with matrixed iodine to provide an anti-infective coating with a rapid release and a sustained release of iodine over a period of weeks. A non-iodized polymer coating may be deposited on the complexed coating, the matrixed coating or the combined coating to provide protection to the sub coating and to further control the rate of release of iodine. The iodine containing coating provides a concentration of iodine that has sufficient activity and is available for a period of time which is long enough to allow germs to be inactivated. The coated device is stable and has long shelf life. The coated device effectively inactivates human immunodeficiency virus. The technology for preparing polymer-iodine complexes, polymer-iodine matrixes and coating combinations is disclosed in our aforesaid U.S. Pat. Nos. 5,344,411 and 5,437,656, the disclosures of which is incorporated herein.

Envisioned by our invention is a polymer-iodine controlled release system that can provide the proper iodine concentration upon demand or for an extended time period by various means, other than by a full surface coating. To be more specific, our invention includes the following forms of delivery:

a. Partial coating of the internal surface of the bag from about 1% to 100% of the surface area that may be in contact with the fluids.

b. Coating of the inner surface of parts in contact with the fluids in the bag such as a connector or tubing.

c. Using a sticker that contains the iodine delivery system to be placed in the inner side of the bag. The tag can be fashioned of a material having coated thereon the polymer-iodine coating or the tag could be made only of the polymer-iodine. The tag could be employed in combination with a polymer-iodine coated surface in order to supply added iodine.

d. External patch; use an external device that contains an antimicrobial agent that will defuse through the bag wall and protect the fluids placed in the bag. In this case, the delivery system can be a coating applied on the outer side of the bag or can be a sticker to be attached on the bag. The rate of antimicrobial availability to the fluids in the bag is determined by the diffusion properties of the bag wall (type of polymer, thickness, etc.).

e. An insert. Insert a device releasing iodine into a common bag. The insert should not interfere with the function of the bag (blocking the connectors or tubing). It can be in a form of a piece of tubing, large beads, a piece of film, etc. These inserts are programmed to release a sufficient amount of an antimicrobial agent when fluids are inserted in the bag.

f. It is to be understood that the surface coatings of polymer-iodine could be complete or partial; and of varying thickness and iodine concentration depending upon need. While the receptacles of this invention are primarily described in terms of plastic; the coatings could be applied to the inner surface of glass containers and the like.

Figure 12:
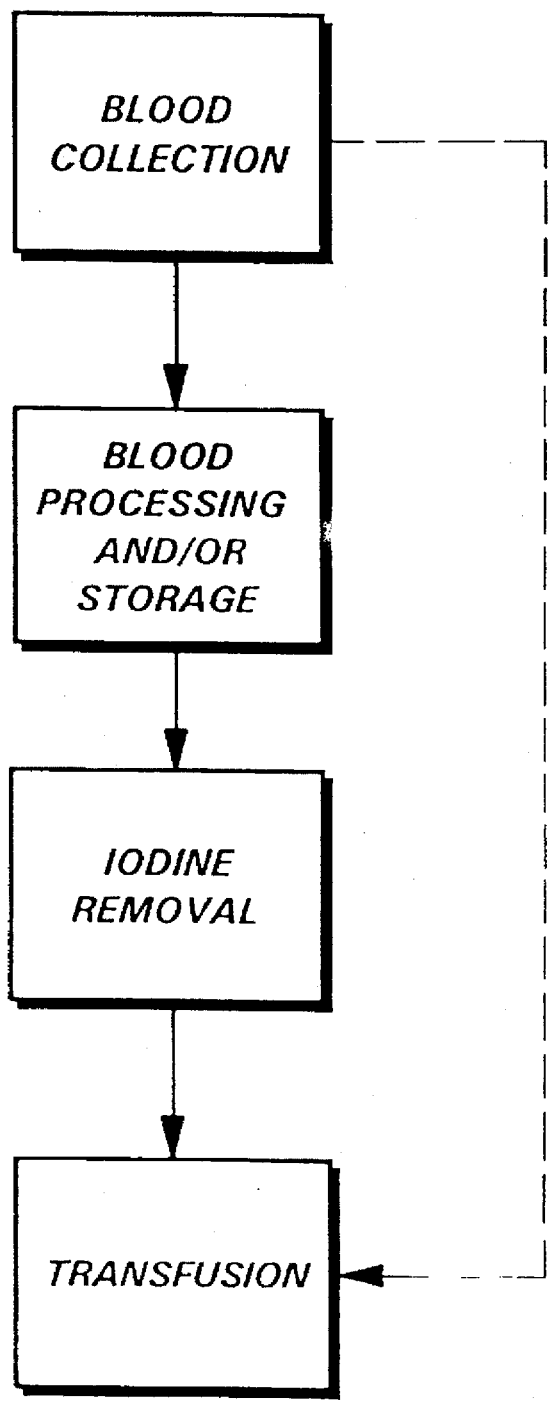
FIG. 12 is a flow chart of process steps that the collected blood can take in the practice of this invention.

Once the blood has been collected, several processing procedures are possible. Referring to FIG. 12, blood is collected, sent to blood processing and/or storage, and iodine can be removed before transfusion. Or the blood can be collected and without being stored the blood can have iodine removed before transfusion. In an alternative process the blood after collection can be fractionated (e.g., separated into red blood cells, white blood cells, platelets etc.) and the needed fraction transfused. The unique and elegant feature of these process steps is the fact that the blood and blood components are brought into contact with the polymer-iodine coating of the blood collection equipment.

As a final step before transfusing the blood, any residual iodine present in the blood or blood fraction can be removed. The removal of the iodine can be by methods known in the art, e.g. chromatography.

The invention contemplates using polymeric coatings that contains a solid solution of iodine in certain polymers. The solution of polymer-iodine mixture is used to coat surfaces of medical devices, as well as non-medical surfaces for antimicrobial and antiviral protection. The selected polymers for our iodine-coating system should perform the following:

1. The polymers must be soluble in organic solvent solutions in order to be coated, cross linked polymers that are insoluble are not useful.

2. The polymers should not adversely chemically react with the iodine.

3. The polymers should be compatible with iodine and form a uniform solid solution or complex with the iodine.

4. The polymer-iodine solution, complex or matrix should form a continuous uniform coating on the applied surface, and should adhere well to the surface.

5. The coating should adhere to the surface and remain stable during storage without significant loss of iodine.

Polymers utilized in the iodine coatings can be polyurea, polyurethane, ethylene vinyl acetate, polyvinylchloride, polyesters, nylon, polycarbonate, polyethylene, polymethyl methacrylate, cellulose esters (like ethyl, methyl and propyl), polypropylene, polystyrene, polytereflouroethylene, polyvinylchloride, poly(ethylenevinyl acetate), elastomeric organosilicon polymers, poly(hydroxy alkyl esters), copolymers and combinations thereof.

The amount of iodine of 0.01% to 0.02% in solution for 30 minutes at 24° C. has been shown to cause inactivation of toxic viruses. In formulating the polymer-iodine coatings of this invention, factors such as the thickness of the coating, the rate of release of iodine from the coating, and substances which may interfere with iodine activity have to be taken into account. Within the starting parameters set forth for iodine inactivation, those skilled in the art will easily be able to formulate effective polymer-iodine coatings for the containers and tubing of this invention.

The thickness of the polymers could be varied from 0.001 inch to several millimeters (e.g. 0.1 to 0.22 mm). This variation in thickness resulted in different concentrations of iodine being released. In theory, an iodine loading within the polymer of 0.01% to 40% iodine is possible and upon leaching out of the polymer will produce the effective antiinfective concentration.

The polymer-iodine solution can be applied to the surface by dipping, spraying, brush coating ... etc. It is essential that the polymer be selected based on its adherence properties to specific surface materials. In general, surfaces of certain polymeric material should be coated with similar polymeric material which fit the requirements listed above. The advantage of the antiinfective polymer coating of this invention is that it has the capacity to release an effective concentration of iodine in sustained fashion for prolonged periods of time; hence assuring the long exposure of the organism to iodine. The medical device can be precoated with the polymer loaded with iodine (or in an emergency the polymer-iodine can be applied immediately before the device is used, as for example, by a spray). The iodine will begin to be released when the device is exposed to the contaminated fluid. Before being exposed to fluid, the coated device is inert and stable in shelf conditions for at least two years.

It is quite evident that it would be difficult to coat receptacles or blood containers once they are formed. This invention envisions precoating with a polymer-iodine coating the surface of an article before it is formed; and then forming the article into a receptacle, etc. Formed articles, however, could be dipped into the polymer-iodine for coating.

This invention also describes dispersions and solutions of polymeric iodophors (polymer and "hold" iodine) that can be applied as coating on blood-contacting medical devices and medical goods for sanitation purposes. The liquid preparations can be applied by spraying, brushing, rolling, etc. of the solution on the desired surface to form a uniform coating containing iodine. The iodine is trapped in the coating material and is released when it comes in contact with aqueous liquids, such as blood, body fluids and water.

Two types of sprays are proposed. The first class of spray is one based on organic solvents such as ethanol, aliphatic ketone (i.e. dimethyl ketone), tetrahydrofuran (THF) and chlorinated hydrocarbons. The second class are solution or dispersions in water and mixtures with organic solvents.

Preparation of spray solution in THF

To 1% w/v solution of segmented polyurethane (Pellethane or Tchoflex) in THF, 0.4 grams of elemental iodine is added and mixed until all iodine is dissolved. The solution is then loaded into a spray can. Spraying the solution onto a polyurethane surface resulted in a uniform thin brown coating. Solutions of up to 10% polymer load are prepared. These solutions can also be applied by casting or brushing to result in uniform coating.

Preparation of spray solution in ethanol

To 80 ml ethanolic solution containing 2% w/v of ethyl cellulose, 20 ml 1% ethanolic solution of polyvinyl-pyrrolidone:iodine complex is added and mixed well using sonication or homogenization. The solution is then charged into a spray can and applied on a PVC surface to form a uniform light-brown coating which adheres well to the surface. A uniform coating can be obtained on metals, as well as polyurethane, polyethylene and polyacrylates. In this application the surface coating polymer is ethyl cellulose; however, other compositions using the same concept may contain other film forming polymers such as, hydroxypropyl-cellulose, as well as other cellulose esters and copolymers of methyl methacrylate and methacrylic acid (eudragit polymers). The compositions may contain up to about 10% of film forming inert polymer and up to 10% of polymeric iodophor. The iodine release rate and duration of effectiveness from the coating is dependent on the amount of sprayed material applied per surface area, the ratio of iodophor to film forming polymer, the iodophor loading, the type of iodophor and film forming polymer and additives such as poly(ethylene glycol), plastisizers such as tributylcitrate and dibutylsebacate.

Preparation of spray solution in water

To an aqueous dispersion of copolymers of methyl methacrylate and methacrylic acid (Eudragit polymer dispersions available from Rohm Pharma) or cellulose esters (Aquacort available from Dow) there is added a solution of povidone-iodine. The mixture is mixed well to form a uniform dispersion suitable for spraying or applying by brush to form a uniform coating on various surfaces. In a typical example, 20 ml of Eudragit S (30% dispersion in water containing tributylcitrate as plasticizer) is mixed with 20 ml of 5% povidone-iodine solution. The mixture is mixed well and water is added to form 100 ml brown dispersion. Coating of this composition (0.002 mm thick) on gauze fabric releases iodine for at least three (3) days when placed in 0.001N KI solution. Iodine content is determined by UV at 303 nm.

Modified polyvinylpyrrolidone-iodine

A copolymer of vinylpyrrolidone and octadecene (1 to 30% octadecene content) is prepared by radical copolymerization. This hydrophobic polymer is less soluble in water but soluble in alcohol and organic solvent. Complexation of iodine is prepared using the method used to make povidone-iodine. The poly(vinylpyrrolidone-octadecene)-iodine [P(VP-OC)-I] is dissolved in alcohol and used for spraying. Alternatively, the polymer forms a colloidal dispersion in water and is used for coating. Because of the hydrophobicity of the copolymer, a water insoluble and water stable coating is obtained which can be removed by alcohol. Copolymers with other hydrophobic aliphatic monomers such as alky-acrylates and vinyl alkanes may be used. Dispersions of solutions of these polymeric iodophors may contain inert film forming polymers or other inert components for the purpose of improving the properties of the coating. These include plastisizers and hydrophilic or hydrophobic polymers.

The rate of release from a coated surface was further shown to be controllable by depositing the polymer/iodine coating on culture cluster plates.

Polyurethane-iodine complex: 24 well culture cluster plates (Costar, Cambridge Mass.) were coated with polyurethane by spreading 50 microliters of polyurethane (PU)

solution in tetrahydrofuran (THF, 2.5 weight %) per well. After solvent evaporation, a uniform thin coating of 0.4 m g/cm$^2$ was obtained. To each well 3 ml iodine-potassium iodide solutions were added and allowed to react for 60 minutes at room temperature. The solutions were discarded and the wells were rinsed with deionized water for 10 minutes and left to dry at room air for 24 hours. The iodine concentrations in the solution were 1.0M, 0.1M, 0.05M, 0.01M, and 0.001M; the potassium iodide concentrations were 1.5 times the molarity of iodine in the solutions. For each concentration a total of four (4) wells were used. The total amount of iodine absorbed in the PU-iodine complex was 4, 1, and 0.5 weight % (50, 12 and 5 microgram per well), based on the polyurethane coating, from 1, 0.1, and 0.05M iodine solution, respectively. The 0.01M and 0.001M solutions did not provide detectable amounts of iodine.

Iodine release was studied by adding into the wells 3 ml phosphate buffer pH 7.4 at 37° C., or in 0.01M potassium iodide solution at 25° C. The solutions were replaced frequently with fresh solutions and the iodine concentrations in the solutions were determined by UV absorption at 280 nm.

Figure 13:
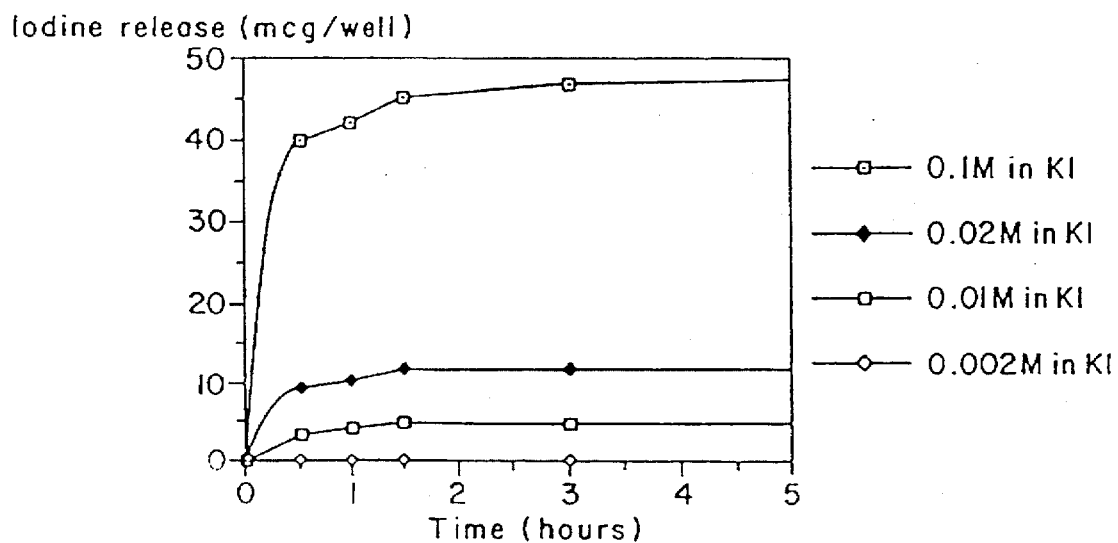
FIG. 13 is a graph of the rate of iodine release from a polymer iodine complex in potassium iodide.

The in-vitro release from polyurethane-iodine complex was rapid both in phosphate buffer and in potassium iodide solution. In phosphate buffer pH 7.4 at 37° C., iodine was released rapidly from the coating with about 90% of the iodine released in 3 hours, the remaining 10% was released constantly in the following 48 hours. The release in potassium iodide solution was even faster and 90% of the iodine content was released in 1 hour. The increase in iodine release in potassium iodide solution was due to the higher solubility of iodine in potassium iodide solution (FIG. 13).

Having demonstrated that the catheters can be effectively coated with a polymer that is programmed to release iodine for periods that are long enough and at concentrations that are high enough to theoretically inactivate the HIV virus, the next experiment consists of effectively proving that the programmable-iodine releasing polymer is about to inactivate the virus. The programmable iodine-loaded polymer was tested using culture plates that are usually used in viral cultures.

Polyurethane-iodine matrix: 24 well plates (Costar) were coated with polyurethane-iodine by spreading 50 microliters of polyurethane-iodine (PU-iodine) solution in tetrahydrofuran (THF, 2.5 weight %) in each well. After solvent evaporation a dark coating was obtained. The iodine concentration in the polyurethane coating was 10, 20, and 30% based on the polyurethane. The total iodine content in the PU-iodine matrices was 120, 240 and 360 micrograms of iodine per well for the 10, 20 and 30 weight % PU-iodine coating. For each concentration, four wells were used.

Figure 14:
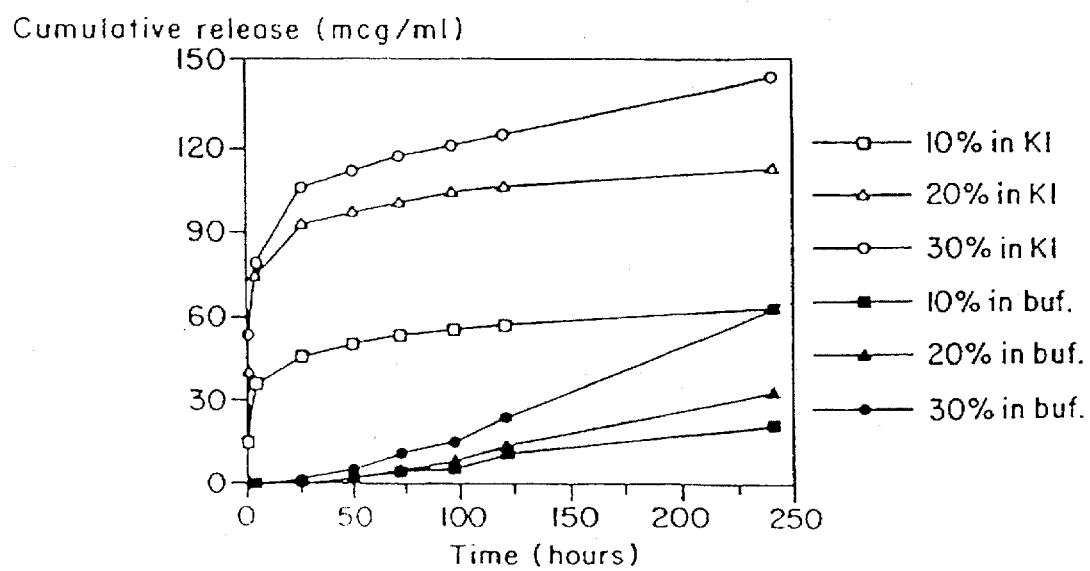
FIG. 14 is a graph of the rate of iodine release from a polymer-iodine matrix in potassium iodide.

The release of iodine from the polyurethane-iodine matrix in phosphate buffer was very slow and was dependent on the solution in which the polymer is placed. In phosphate buffer solution, a negligible amount of iodine was released in 3 days. On the other hand, in potassium iodide solution, a significant amount of iodine was released for 10 days. About 70 to 80% of the iodine was released in 24 hours, and the rest was released constantly over a period of more than 10 days (FIG. 14).

By changing the thickness of the polymer coating and by using more than one polymer coating (e.g. using a combination of polyurethane-iodine matrix or polyurethane-iodine complexes, with a second coating of polyurethane-iodine complex or uniodized polymer), the amount and duration of iodine release can be programmed at the time of the coating. Using this approach, the duration of iodine release can be sustained for up to several months.

The effectiveness of the polyurethane-iodine coating has been demonstrated with HIV virus grown in tissue culture plates that have been coated with the complex coating of the present invention.

The in-vitro anti- HIV activity of the polyurethane-iodine coated plates was assessed by incubating HIV-3B virus in coated plates for 15 minutes, 30 minutes, 90 minutes, 3 hours, 6 hours, 12 hours and 24 hours prior to infection of the human lymphocyte (MT4) cells (5×100,000 cells/ml) at a multiplicity of infection of 100×tissue culture infections dose (TCID) 50. The plates were coated with polymers that release different concentrations of iodine; 1.8, 5.8, 7.3, and 9.2 µg of iodine/ml/hr. for at least the first few hours. The virus, and thus the coated plates, were diluted 1:20 before adding the cells. The infection was allowed to incubate at 37° C. for one hour, at which time the cells were diluted with culture medium RPM1 1640 supplemented with 10% heat-inactivated fetal bovine serum and 10% interleukin2 to a cell density of 8×10,000 cells/ml. The cells were then seeded onto 96-well plates and incubated at 37° C. Five days later, the cell-free supernatant was analyzed for reverse transcriptase and cells infected with virus exposed to plates coated with the present invention for 24 hours were analyzed for cell growth.

The MT4 cells that were exposed to the polyurethane-iodine complex multiplied as rapidly as control non-infected cells, indicating complete inactivation of the HIV.

Figure 15:
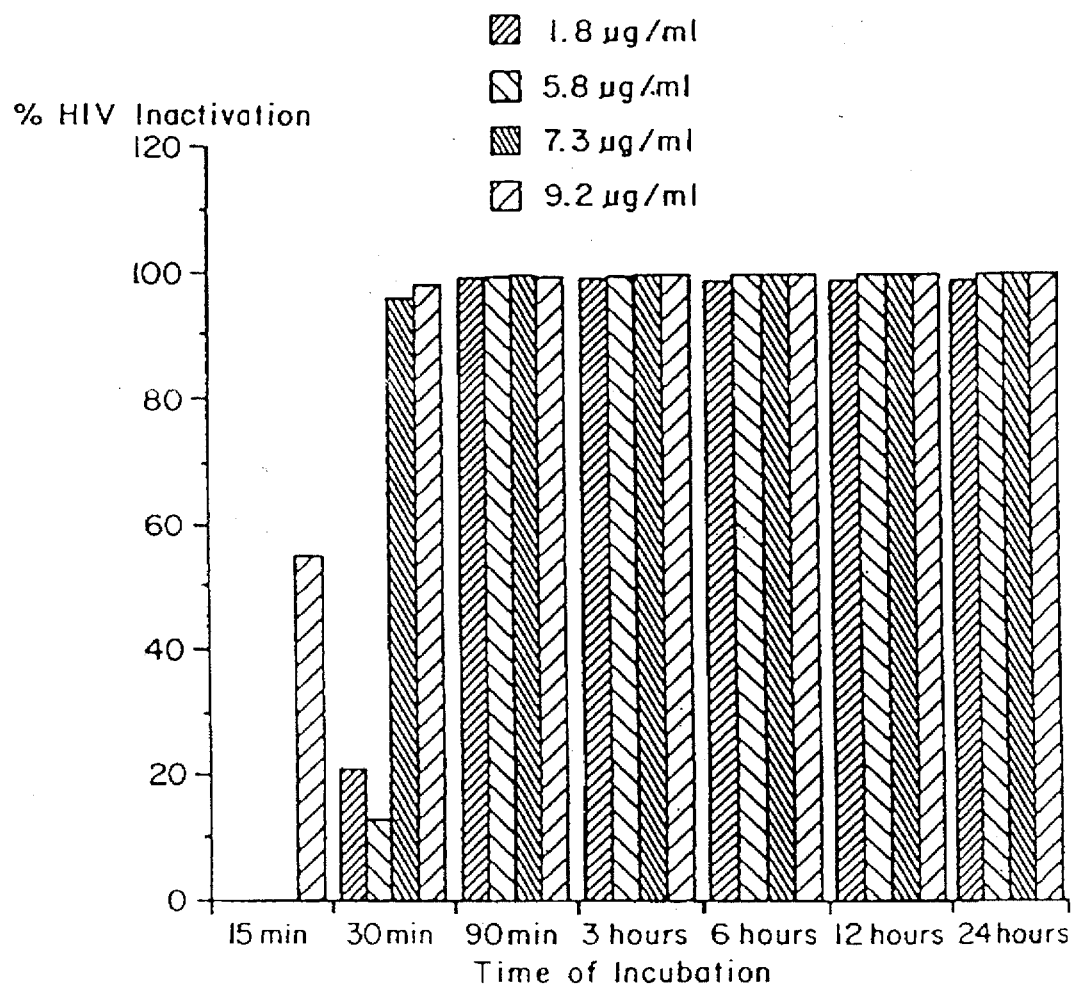
FIG. 15 is a bar graph of the inactivation of HIV virus by the coating of the present invention.

A quantitative analysis of the HIV inactivation was done in the polyurethane-iodine complex plates, by analyzing the cell-free supernatant for reverse transcriptase (RT). The data are summarized in FIG. 15.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for the safe and effective collection, storage and transfusion of blood comprising the steps of, collecting blood from a donor into a polymer-iodine coated container to receive said blood, storing said collected blood in a polymer-iodine coated storage container prior to transfusion, and then transfusing into a recipient the blood from a polymer-iodine coated transfusion container, wherein the iodine released from each polymer-iodine coated container aids in inactivating toxic microorganisms in said blood.

2. The method of claim 1, wherein the iodine is removed from the stored blood prior to the transfusing.

* * * * *